United States Patent [19]

Richman

[11] 4,050,121

[45] Sept. 27, 1977

[54] SINGLE SUBSTRATE TAB FASTENER

[75] Inventor: Edward B. Richman, Shaker Heights, Ohio

[73] Assignee: Avery International Corporation, San Marino, Calif.

[21] Appl. No.: 757,910

[22] Filed: Jan. 10, 1977

[51] Int. Cl.$^2$ ............................................. A44B 21/00
[52] U.S. Cl. ................................. 24/73 VA; 428/41; 128/287; 24/67 AR
[58] Field of Search ............... 24/7, 204, DIG. 11, 24/DIG. 18, 67 R, 73 VA, 67 AR; 128/DIG. 15, 287, 284; 428/41

[56] References Cited

U.S. PATENT DOCUMENTS

| 3,869,761 | 3/1975 | Schaar | 24/73 VA |
| 3,931,666 | 1/1976 | Karami | 24/73 VA |

Primary Examiner—G. V. Larkin
Attorney, Agent, or Firm—McNenny, Pearne, Gordon, Gail, Dickinson & Schiller

[57] ABSTRACT

A linerless diaper tab is formed of a single substrate which can be folded and refolded on itself in such a way as to (1) grip both sides of one part of a diaper adjacent an edge thereof and (2) provide linerless protected storage of an adhesive surface which is exposable for adherence to another part of the diaper, and (3) provide a resultant high-strength Y-configuration fastening between the two parts of the diaper.

8 Claims, 11 Drawing Figures

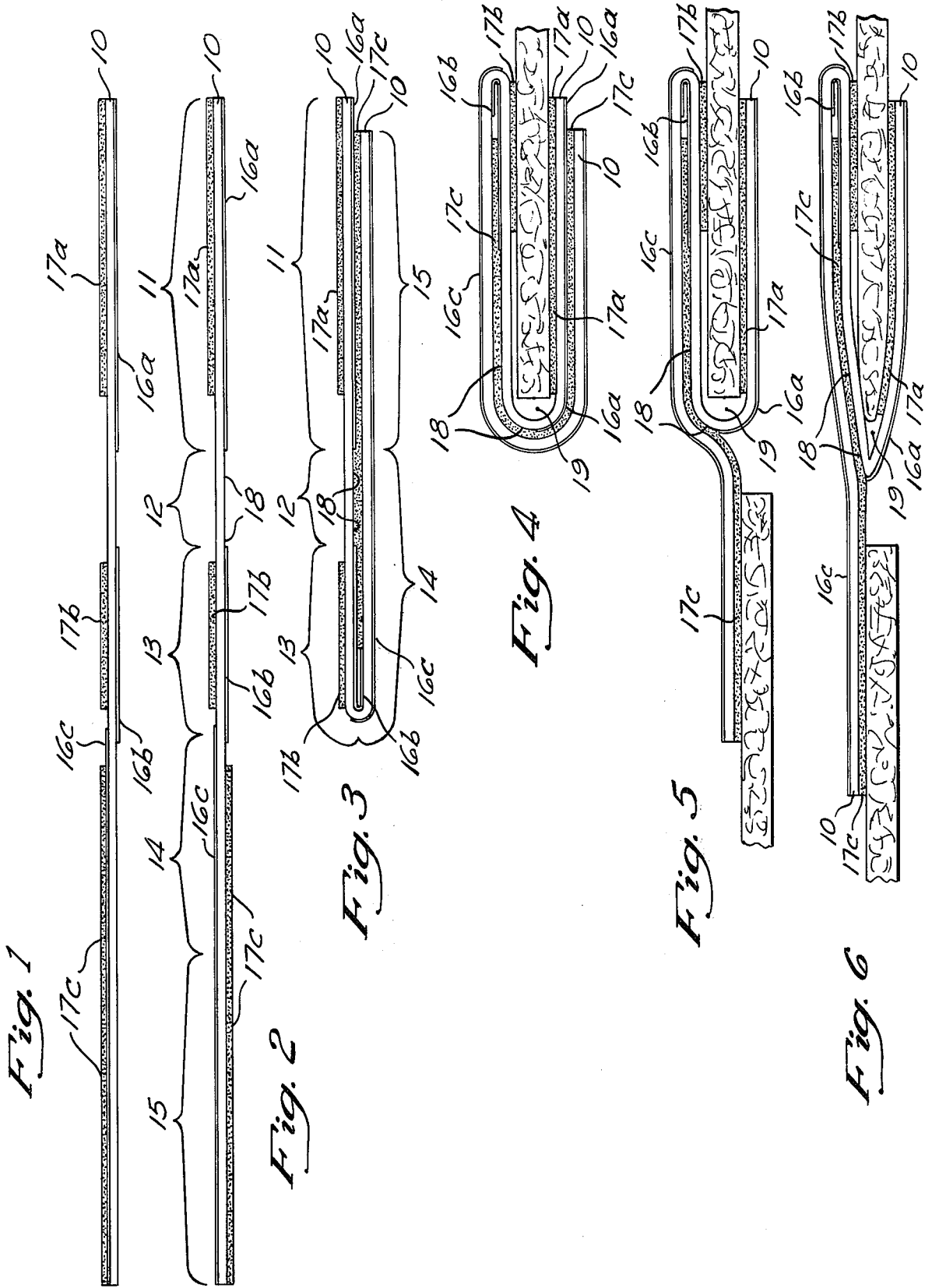

SINGLE SUBSTRATE TAB FASTENER

This invention relates to web constructions of linerless tab stock of the kind adapted to be supplied to a diaper manufacturer and to be separated by the manufacturers into individual diaper tab constructions of Y-configuration and applied to individual diapers, usually two tabs to a diaper. By "linerless" is meant the absence of any adhesive-protecting liner of release paper or the like that has to be separately disposed of by the person applying the diaper. By "Y-configuration" is meant a tab configuration in the shape of a Y whose two legs and stem all bear adhesive, the legs being adapted to the fastened by the manufacturer to both sides of one part of a diaper adjacent an edge, and the stem being adapted to be fastened to another part of the diaper by a person applying the diaper. Tabs of Y-configuration provide increased or doubled strength where it is most needed — at the diaper-to-tab connection which receives the strain when the person applying the diaper pulls on the tab to draw the diaper tight before closing it.

Prior examples of tabs of Y-configuration are Reed et al. U.S. Pat. No. 3,833,456 issued to Avery Products Corporation (common assignee) and Buell U.S. Pat. No. 3,848,594 issued to The Procter & Gamble Company. The former is linerless while the latter is not.

Up to the present time all diaper tab stock suitable for forming tabs of Y-configuration, whether linerless or not, has comprised multiple substrates laminated together into a laminate web construction.

Non-laminate or single substrate linerless constructions are proposed, or at least referred to, in the following patents:

| | | | |
|---|---|---|---|
| 3,853,129 | 12/1974 | Kozak | Union Carbide Corporation |
| 3,874,386 | 4/1975 | Kozak | Union Carbide Corporation |
| 3,930,503 | 1/1976 | Tritsch | Johnson & Johnson |
| 3,955,576 | 5/1976 | Safford | Kimberly-Clark Corporation. |

However none of such constructions provide a Y-configuration.

Other prior art includes:

| | | | |
|---|---|---|---|
| 3,616,114 | 10/1971 | Hamaguchi et al. | Daiel Shikogyo Kabushiki Kaisha; Tanaka-ya Shojii Kabushiki Kaisha; and Sekisui Kagaku Kogyo Kabushiki Kaisha |
| 3,950,824 | 4/1976 | Karami | The Kendall Company |
| Appl. Ser. No. 624,870 | Filed 10/1975 | Richman et al. | Avery Products Corporation (common assignee) |
| Appl. Ser. No. 743,640 | Filed 11/1976 | Nemeth et al. | Avery International Corporation (common assignee) |

Application Ser. No. 624,870 is now U.S. Pat. No. 4,020,842.

The present invention provides, for the first time, a nonlaminate or single substrate linerless tab stock for forming tabs of Y-configuration. The diaper tab stock can be fabricated of a single initially flat but flexible substrate and completely by web coating and slitting steps and without any laminating or folding by the fabricator of the diaper tab stock. The tab stock so made may be adpated to be self-wound for storage and shipment. The result is the achievement of substantial economies and efficiencies in the manufacture of diaper tab stock for tabs of Y-configuration, and in the manufacture and application of tabs formed from such stock.

In the drawings,

FIG. 1 is a diagrammatic cross-sectional view of a coated substrate which may be used in the manufacture of a web construction contemplated by the invention.

FIG. 2 is a similar view of a web construction resulting from self-winding and then unwinding the coated substrate FIG. 1.

FIGS. 3 and 4 illustrate successive stages in the folding and application to a diaper of the web construction of FIG. 2. FIG. 4 may also be viewed as a side elevation of one form of individual diaper tab as applied on a diaper by a diaper manufacturer.

FIGS. 5 and 6 illustrate the use of the diaper tab seen in FIG. 4.

FIG. 8 may also be viewed as a side elevation of another form of individual diaper tab as applied on a diaper by a diaper manufacturer.

Figure 7:
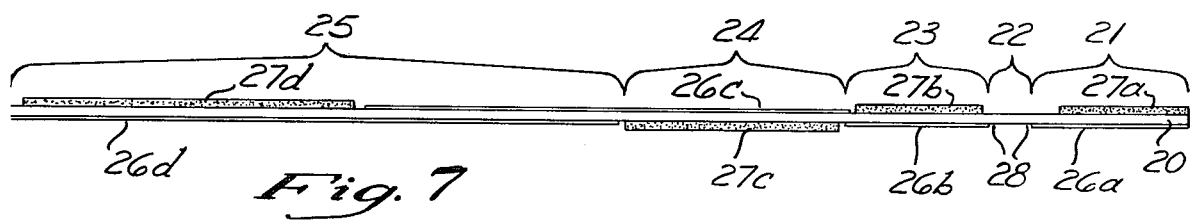
FIG. 7 is a view of another web construction contemplated by the invention.

In FIG. 1 a substrate 10 is coated with release coatings 16a, 16b and 16c and with pressure sensitive adhesive coatings 17a, 17b and 17c. When this construction is self-wound and then unwound, the adhesive 17c transfers from the top to the bottom of the construction to provide the linerless diaper tab stock illustrated in FIG. 2. The winding of the stock may be done by the manufacturer of the diaper tab stock, and the unwinding may be done by the diaper manufacturer shortly before use of the stock in providing tabs for diapers.

In the web construction shown in FIG. 2, the substrate 10 extends, transversely to machine direction, along first, second, third, fourth and fifth endwise length portions labeled respectively 11, 12, 13, 14 and 15. The first and third length portions 11 and 13 include adhesive on the top side of the substrate and release means on the bottom side. The second length portion 12 has no release means on the bottom side of the substrate and thereby defines an anchoring portion 18 where release means is absent. Preferably, the second length portion 12 has no adhesive on the top side and the adhesive 17a on the top side of the first length portion 11 terminates short of the release coat 16a on the bottom side, as shown.

The fourth length portion 14 is sufficiently wide for the bottom side of the substrate 10 at the fourth length portion 14 to be folded across the third portion 13 and reach and at least partially cross the anchoring portion 18 provided at the second length portion 12 and preferably completely cross it as seen most clearly in FIG. 3. The fourth length portion 14 has adhesive 17c on the bottom side of the substrate 10 and release means 16c on the top side of the substrate 10 at at least the part of the fourth length portion 14 which is capable of crossing the anchoring portion 18 when the fourth length portion 14 is folded across the third length portion, as will be understood from a study of FIGS. 2 and 3. The fifth length portion 15 also includes adhesive 17c and release means 16c on opposite sides of the substrate. In the embodiment of FIGS. 1 through 6, the length portions 14 and 15 are both provided with adhesive on the same side of the substrate 10. At least the endmost portion of the adhesive 17c associated with the fifth length portion 15 is releasably supportable on the release means 16a of the first length portion 11 as seen in FIGS. 3 and 4, and can be released therefrom as seen in FIGS. 5 and 6.

The total length of the fourth and fifth length portions 14 and 15 is substantially equal to or slightly less than the total length of the first three length portions 11, 12 and 13. Preferably the total length is slightly less so as to form a slight step or pick-off between the two ends of the substrate 10 as seen in FIGS. 3 and 4.

When the diaper tab stock is unwound by a diaper manufacturer in the configuration of FIG. 2, it can then be folded once to give the configuration of FIG. 3 and then folded again around a diaper edge while or immediately after being severed into an individual diaper tab by a transverse cut across the substrate 10 forming one of a successive series of cuts forming a succession of diaper tabs. Folding around the diaper is preferably done so as to form a gap 19 which is adhesive-free on the diaper side due to termination of the adhesive 17a short of the termination of the release coat 16a and the absence of adhesive on the originally top side of the substrate at the first and second length portions in the vicinity of the termination of the release coat 16a, as previously described.

To fasten a diaper, a parent can lift the end of the tab associated with the fifth length portion, pull it to draw the diaper tight, and press the fifth length portion against another part of the diaper to be joined, as seen in FIG. 5. The diaper tab thereby assumes a Y-configuration. The two legs of the Y at the righthand part of the construction as viewed in FIGS. 5 and 6 provide increased strength when the person applying the diaper pulls on the tab to draw the diaper tight before closing it with the free end of the tab. FIG. 6 illustrates the sharing of the pulling forces between both legs of the Y. The pulling forces are transmitted to the stem of the Y through the anchoring portion 18 and particularly that part thereof closest to the point where the Y branches or divaricates. The termination of release coat 16a determines the point of divarication, which is away from the edge of the diaper due to the gap 19. This fact, and the absence of adhesive on the diaper side of the substrate 10 at the gap 19, contribute to the sharing and balancing of the pulling forces between both legs of the Y, since the legs are free to independently stretch or adjust as required to best share the pull imposed on the tab and distribute such pull to both sides of the diaper portion that is gripped by the legs of the Y. This feature in itself is not broadly novel, but is an advantageous characteristic of tabs of the Y-configuration type. However it is not believed to have been previously achieved in single substrate constructions.

Thus it will be seen that diaper tab stock of the Y-configuration type has been provided from a non-laminate or single substrate linerless tab stock which itself can be fabricated completely by web coating and slitting steps and without any laminating or folding by the fabricator of the diaper tab stock, such construction also being adapted for self-winding for storage and shipment. Such construction realizes substantial economies and efficiencies in the manufacture of diaper tab stock for tabs of Y-configuration. The diaper tab manufacturer may readily and efficiently use such stock in the manufacture and application of Y-configuration tabs.

Figure 8:
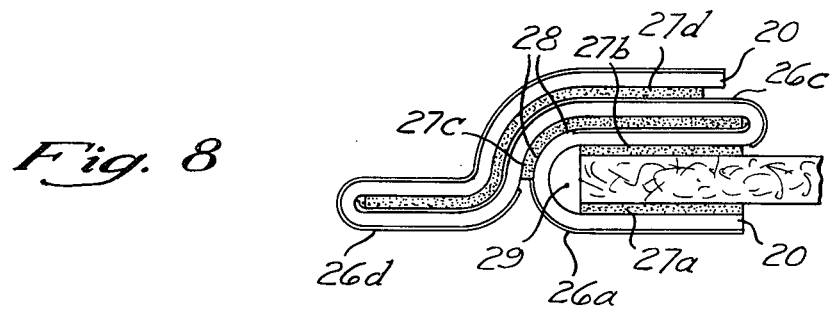
FIG. 8 is a view on a slightly enlarged scale of the application of the construction of FIG. 7 to a diaper.
Figure 9:
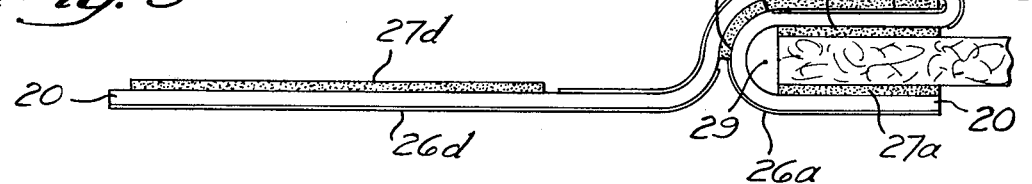
FIGS. 9 and 10 illustrate the use of the diaper tab seen in FIG. 8.
Figure 10:

Another embodiment of the invention is shown in FIGS. 7 through 11. In the web construction shown in FIG. 7, the substrate 20 extends transversely to machine direction along first, second, third, fourth and fifth endwise length portions labeled respectively 21, 22, 23, 24 and 25. The first and third length portions 21 and 23 include adhesive 27a and 27b on the top side of the substrate and release means 26a and 26b on the bottom side. The second length portion 22 has no release means on the bottom side of the substrate to thereby define an anchoring portion 28 where release means is absent. The fourth length portion 24 is sufficiently wide for the bottom side of the substrate 20 at the fourth length portion 24 to be folded across the third length portion 23 and reach at least partially across the anchoring portion 28 provided at the second length portion 22. The fourth length portion 24 has adhesive 27c on the bottom side of the substrate 20 and release means 26c on the top side of the substrate 20 at at least the part of the fourth length portion 24 which is capable of crossing the anchoring portion 28 when the fourth length portion 24 is folded across the third length portion, as will be understood from a study of FIGS. 7 and 8. The fifth length portion 25 also includes adhesive 27d and release means 26d on opposite sides of the substrate. In the embodiment of FIGS. 7 through 11, the length portions 24 and 25 are provided with adhesive on opposite sides of the substrate 20. At least the endmost portion of the adhesive 27d associated with the fifth length portion 25 is releasably supportable on the release means 26c of the fourth length portion 24, as seen in FIG. 8, and can be released therefrom as seen in FIGS. 9 and 10.

In this embodiment, the diaper manufacturer must fold the diaper tab stock three times as illustrated in FIG. 8, one fold being around the diaper and the other two folds being folds of the construction on itself. These folds should be made by the manufacturer before severing the stock into individual diaper tabs and the folds which embraces the edge of the diaper may be preformed prior to actual engagement of the diaper so that severance into individual tabs may occur without severing the diaper edge.

Figure 11:
FIG. 11 is a view similar to FIG. 10, with the diaper tab being shown on a scale more nearly in proper proportion to the diaper.

The tab as applied to the diaper by the manufacturer has the configuration of FIG. 8. Again as in the earlier embodiment, an adhesive free gap is formed, as at 29. To fasten a diaper, a parent can lift the end of the tab associated with the fifth length portion as seen in FIG. 9 and position the fifth length portion in association with another part of the diaper to be joined as seen in FIG. 10. The diaper tab thereby assumes a Y-configuration. The two legs of the Y at the righthand part of the construction as viewed in FIGS. 9 and 10 provide increased strength when the person applying the diaper pulls on the tab to draw the diaper tight before closing it with the free end of the tab. FIG. 10 illustrates the sharing of the pulling forces between both legs of the Y. The pulling forces are transmitted to the stem of the Y through the anchoring portion 28 and particularly that part thereof closest to the point where the Y branches or divaricates. Again, as in the previous embodiment, the termination of the release cost (in this case release coat 26a) determines the point of divarication which, due to the gap (29 in this case) is spaced from the diaper edge. Again, pulling forces tend to be shared and balanced between the two legs of the Y. FIG. 11 illustrates the configuration of the tab under pulling stress, with the tab being shown on a scale more nearly in proper proportion of the diaper.

Thus it will be seen that diaper tab stock of the Y-configuration type has again been provided from a non-laminate or single substrate linerless tab stock which itself can be fabricated completely by web coating and slitting steps and without any laminating or folding by the fabricator of the diaper tab stock, such construction also being adapted for self-winding for storage and shipment. However, the embodiment of FIGS. 7 through 11 involves more folds than the previously described embodiment and a more intricate pattern of web coatings on the substrate. Accordingly the embodiment of FIGS. 1 through 6 is presently preferred over the embodiment of FIGS. 7 through 11.

The invention is not restricted to the specific details of the disclosed embodiments but is defined in the following claims.

What is claimed is:

1. A web construction of linerless diaper tab stock made up of a single flat but flexible coated substrate suitable to be formed in long passes along the machine direction of a coating and laminating line and to be rolled up for storage and shipment, and unrolled for use by diaper manufacturers, and fabricatable completely by web coating and slitting operations and without the necessity for laminating or folding operations, and suitable for high speed dispensing on automatic equipment, including a substrate extending, transversely to machine direction, along first, second, third, fourth and fifth endwise length portions, said first and third length portions including adhesive on the top side of the substrate and release means on the bottom side, said second length portion having no release means on the bottom side of the substrate to thereby define an anchoring portion where release means is absent, said fourth length portion being sufficiently wide for the bottom side of the substrate at the fourth length portion to be folded across said third length portion and reach and at least partially cross said anchoring portion, said fourth length portion having adhesive on the bottom side of the substrate and release means on the top of the substrate at at least the part of the fourth length portion which is capable of crossing said anchoring portion when said fourth length portion is so folded, said fifth length portion including adhesive and release means on opposite sides of the substrate.

2. A device as in claim 1 in which the fourth length portion is sufficiently wide for the bottom side of the substrate at the fourth length portion to be folded across the third length portion and reach entirely across said anchoring portion.

3. A device as in claim 2 in which the adhesive on the top side of the substrate at the first length portion terminates short of the point at which the release means on the bottom side thereof terminates and the top side of the substrate at the second length portion is free of adhesive at least at the part of the second length portion that is adjacent the first length portion.

4. A device as in claim 3 in which the adhesive of the fifth length portion is on the same side of the substrate as the adhesive of the fourth length portion.

5. A device as in claim 4 in which at least the endmost portion of the adhesive of the fifth length portion is releasably supportable on the release means of the first length portion.

6. A device as in claim 5 in which the total length of the fourth and fifth length portions is substantially equal to or slightly less than the total length of the first three length portions.

7. A device as in claim 3 in which the adhesive of the fifth length portion is on the opposite side of the substrate from the adhesive of the fourth length portion.

8. A device as in claim 7 in which at least the endmost portion of the adhesive of the fifth length portion is releasably supportable on the release means of the fourth length portion.

* * * * *

UNITED STATES PATENT AND TRADEMARK OFFICE
CERTIFICATE OF CORRECTION

PATENT NO. : 4,050,121
DATED : September 27, 1977
INVENTOR(S) : Edward B. Richman It is certified that error appears in the above-identified patent and that said Letters Patent are hereby corrected as shown below:

Column 2, line 9, after "substrate" add --of--.

Column 2, line 55, after "third" add --length--.

Column 4, line 61, change "cost" to --coat--.

Claim 1, column 6, line 2, after "top" add --side--.

Signed and Sealed this

Seventh Day of February 1978

[SEAL]

Attest:

RUTH C. MASON
Attesting Officer

LUTRELLE F. PARKER
Acting Commissioner of Patents and Trademarks